United States Patent [19]

Hisamitsu et al.

[11] Patent Number: 4,673,744
[45] Date of Patent: Jun. 16, 1987

[54] METHOD FOR CONVERSION OF β-ASPARTYLPHENYLALANINE DERIVATIVES TO α-ASPARTYLPHENYLALANINE DERIVATIVES

[75] Inventors: Kunio Hisamitsu, Funabashi; Tadashi Takemoto; Toshihide Yukawa, both of Yokohama, all of Japan; Kunio Hisamitsu, Funabashi

[73] Assignee: Ajinomoto Co., Inc., Tokyo, Japan

[21] Appl. No.: 857,978

[22] Filed: May 1, 1986

[30] Foreign Application Priority Data

Jun. 4, 1985 [JP] Japan .................... 60-121124

[51] Int. Cl.$^4$ .................................. C07D 24/08
[52] U.S. Cl. ................................ 544/385; 560/24; 562/442
[58] Field of Search .................. 544/385; 560/24; 562/442

[56] References Cited

U.S. PATENT DOCUMENTS 3,560,503  2/1971  Anand et al. ................ 544/385
4,088,649  5/1978  Smith et al. ................ 544/385

Primary Examiner—Glennon H. Hollrah
Assistant Examiner—James H. Turnipseed
Attorney, Agent, or Firm—Oblon, Fisher, Spivak, McClelland & Maier

[57] ABSTRACT

A method for converting β-aspartylphenylalanine derivative (1) to α-aspartylphenylalanine derivatives (2) and (3), said derivatives having the following structures:

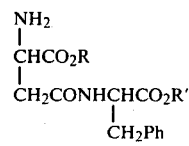

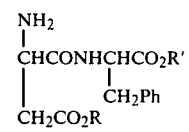

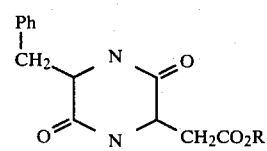

which comprises:
reacting said β-aspartylphenylalanine derivative (1) at a temperature of from 0° to 200° C. for a time period of from 30 minutes to 80 hours, in a $C_1$ to $C_4$ alcohol solvent with or without stirring, wherein R and R' represent hydrogen or an alkyl group having from 1 to 4 carbon atoms.

3 Claims, No Drawings

METHOD FOR CONVERSION OF β-ASPARTYLPHENYLALANINE DERIVATIVES TO α-ASPARTYLPHENYLALANINE DERIVATIVES

DETAILED EXPLANATION OF THE INVENTION

The present invention relates to a method for conversion of a β-aspartylphenylalanine derivative 1 into α-aspartylphenylalanine derivatives 2 and 3 (α-aspartylphenylalanine anhydride derivatives) efficiently in accordance with the reaction equation described below:

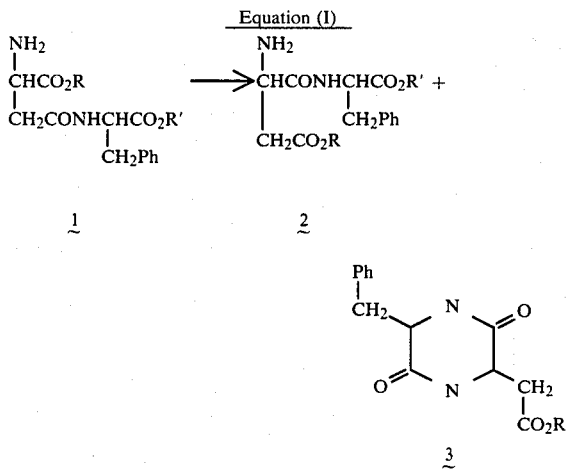

wherein R and R' represent hydrogen or an alkyl group having 1 to 4 carbon atoms.

Various processes for preparing α-L-aspartyl-L-phenylalanine methyl ester (hereafter simply referred to as α-APM) useful as a novel sweetening agent are known.

Examining these processes, most of them comprise protecting the amino group of L-aspartic acid (L-Asp) in any manner, for example, with a carbobenzoxy group, a formyl group, a hydrogen halide, etc., converting it into the anhydride, condensing the anhydride with L-phenylalanine methyl ester (PM) to synthesize N-protected-L-aspartyl-L-phenylalanine methyl ester and removing the protective group to obtain the desired α-APM. However, by production of β-L-aspartyl-L-phenylalanine methyl ester (hereafter simply referred to as β-APM) is unavoidable as far as these processes are used.

In general, by-produced β-APM or its related compounds are hydrolyzed and recovered as L-Asp and L-phenylalanine (L-Phe) which are again used as raw materials.

Accordingly, if β-APM or related compounds could be directly converted into α-APM or related compounds capable of leading to α-APM without hydrolyzing them, such is extremely advantageous.

As a result of extensive investigations with an attempt to convert β-APM and its related compounds (refer to compounds of 1 in the reaction equation above; hereafter simply referred to as β-AP derivatives) into α-aspartylphenylalanine derivatives [refer to compounds of 2 and 3 (compound of 3 is α-aspartylphenylalanine anhydride derivatives; hereafter simply referred to as DKP derivatives) in the reaction equation above; hereafter simply referred to as α-AP derivatives], the present inventors have found that by maintaining the β-AP derivative in an alcohol solvent, it can easily be converted into the α-AP derivatives surprisingly and, have thus come to accomplish the present invention.

As shown in the reaction equation above, the α-AP derivative 1 can be converted into the α-AP derivatives (2 and 3) by maintaining the β-AP derivative in an alcohol solvent with or without stirring, according to the reaction. Further it is known that by treating with hydrochloric acid in an aqueous methanol solution, the obtained α-AP derivatives (2 and 3) are led to α-APM hydrochloride (hereafter simply referred to as α-APM.HCl) (cf. Published Unexamined Japanese Patent Application No. 219258/84 and Published Unexamined Japanese Patent Application No. 174799/85; for reference, Published Unexamined Japanese Patent Application No. 174799/85 is directed to a process for preparing α-L-aspartyl-L-phenylalanine methyl ester which comprises contacting 3-benzyl-6-carboxymethyl-2,5-diketopiperazine with a strong acid in a solvent mixture for a time period sufficient to cause partial hydrolysis). Further α-L-aspartyl-L-phenylalanine methyl ester can also be prepared from 3-benzyl-6-carbomethoxymethyl-2,5-diketopiperazine in a similar manner.

As raw materials used, the β-AP derivative 1 shown in the reaction equation above can generally be used. Among them, particularly advantageously used are β-aspartylphenylalanine dimethyl ester (wherein α-carboxyl group in the aspartic acid residue of β-aspartylphenylalanine methyl ester is converted into methyl ester; hereafter simply referred to as β-APM$_2$) and β-aspartylphenylalanine-α-methyl ester (α-carboxyl group in the aspartic acid residue of β-aspartylphenylalanine is converted into methyl ester; hereafter simply referred to as β-A(M)P).

For reference the β-AP derivative 1 can be obtained as follows, for example.

In case that R is hydrogen among the β-AP derivatives 1 shown in Equation (I), α-carboxyl group of aspartic acid is protected with an ester that can be removed in a manner other than saponification with an alkali, for example, a protective group such as benzyl ester and the N-terminal is protected with a protective group conventionally used. This N-protected-aspartic acid-α-benzyl ester is reacted with phenylalanine alkyl esters in the presence of a condensing agent such as dicyclohexylcarbodiimide to synthesize N-protected-aspartylphenylalanine alkyl ester-α-benzyl ester. Then, the N-protective group is removed in a conventional manner and then the benzyl ester is removed by catalytic reduction to obtain the β-AP derivatives.

Further in case that R and R' are both alkyl groups in the β-AP derivative 1, the product can be obtained by protecting α-carboxyl group of aspartic acid and carboxyl group of phenylalanine with alkyl esters, condensing in the manner described above and removing the N-protective groups.

Further in case that R and R' are both hydrogens in the β-AP derivative 1, the product can be obtained by saponification of any of the alkyl esters of the three described above with an alkali.

The solvent is not particularly limited but preferred are alcohols such as methanol, ethanol, propanol, isopropanol, butanol, etc. Of course, a solvent mixture of a solvent such as ethyl acetate, etc. compatible with the alcohol and causing no obstacle in the reaction according to the reaction equation described above and the alcohol may also be used; such a solvent mixture is also included in the alcohol solvent referred to in the present invention.

The amount of the solvent used to the β-AP derivative 1 is not particularly limited but from economical or operational viewpoint accompanied by undissolved crystals, it is desired that the solvent be used in a 1 to 200-fold amount, by weight, based on the β-AP derivative 1.

The reaction of the present invention in accordance with the reaction equation above may proceeds in the absence of any catalyst but the reaction can be accelerated by acid or basic catalysts; it is particularly advantageous to use the basic catalyst.

The basic catalysts used are not particularly limited; mention may be made of organic bases such as triethyl amine, pyridine, etc., inorganic bases such as sodium hydroxide, potassium hydroxide, sodium carbonate, sodium hydrogen carbonate, etc.

Further the acid catalysts used are not particularly limited; mention may be made of organic acids such as acetic acid, benzenesulfonic acid, etc., inorganic acids such as hydrochloric acid, sulfuric acid, phosphoric acid, etc.

The amount of the catalyst used is not particularly limited but the reaction rate increases as the amount of the catalyst used increases. From an economical viewpoint, it is advantageous that the catalyst be used in an amount of 0.5 to 20-fold amount based on the β-AP derivative 1.

The β-AP derivative 1 is maintained in the aforesaid alcohol solvent in the presence of or absence of the catalyst with or without stirring. The temperature (reaction temperature) in the maintenance is chosen from 0° and 200° C.; however, the temperature range of 40° to 150° C. is advantageous because the reaction rate decreases at low temperatures but at high temperatures, decomposition rate of polymerization, etc. increases, etc.

The time period required for completion of the reaction under the aforesaid conditions varies depending upon amount of the catalyst used or temperature for the maintenance but a period of approximately 30 minutes to 80 hours is required.

According to the method of the present invention, the β-AP derivative 1 can easily be converted into the α-AP derivatives (2 and 3). In addition, α-APM can be obtained using the β-AP derivative 1 as a raw material in accordance with the method of the present invention because it is known that these α-AP derivatives (2 and 3) are converted into α-APM.HCl as described above.

To separate the α-AP derivatives (2 and 3) from the reaction solution containing the α-AP derivatives (2 and 3) can be performed by removing the solvent from the reaction solution by distillation followed by a conventional manner such as crystallizing from water, etc.; it is advantageous, however, to convert the α-AP derivatives (2 and 3) into α-APM.HCl or α-APM by the method described above without separating the α-AP derivatives (2 and 3) from the reaction solution containing them.

Hereafter the present invention will be described in more detail with reference to the examples below but is not deemed to be limited to these examples.

EXAMPLE 1

In methanol (hereafter simply referred to as MeOH) was dissolved 5.65 g of β-L-aspartyl-L-phenylalanine dimethyl ester hydrochloride (wherein α-carboxyl group in the L-aspartic acid residue of β-L-aspartyl-L-phenylalanine methyl ester hydrochloride is converted into methyl ester; hereafter simply referred to as β-APM$_2$(L/L).HCl) to make 1 liter of the MeOH solution of β-APM$_2$(L/L).HCl. After the temperature of 50 ml of the obtained MeOH solution of β-APM$_2$(L/L).HCl was elevated to 60° C., 115 μl of triethyl amine (hereafter simply referred to as Et$_3$N) was added thereto to neutralize hydrochloric acid. Then the mixture was reacted at 60° C. for 30 hours with stirring. Thereafter the α-AP derivatives, namely, α-aspartylphenylalanine dimethyl ester (wherein β-carboxyl group in aspartic acid residue of α-aspartylphenylalanine methyl ester is converted into methyl ester; hereafter simply referred to as α-APM$_2$) and α-aspartylphenylalanine anhydride methyl ester (hereafter simply referred to as DKPOMe) were quantitatively determined by high performance liquid chromatography (hereafter simply referred to as HPLC).

As a result, 20.6% (in detail, 14.7% of α-APM$_2$ and 5.9% of DKPOMe) of the α-AP derivatives was formed.

EXAMPLE 2

The temperature of 50 ml of the MeOH solution of β-APM$_2$ (L/L).HCl prepared in Example 1 was elevated to 60° C. and Et$_3$N was added to the solution in a 10-fold mole amount to β-APM$_2$ (L/L).HCl. The mixture was reacted at 60° C. with stirring.

Twenty-four hours after, the α-AP derivatives were quantitatively determined by HPLC and the α-AP derivatives were formed in 88.8% (in detail, 5.6% of α-APM$_2$ and 83.2% of DKPOMe).

EXAMPLE 3

The MeOH solution of β-APM$_2$(L/L).HCl prepared in Example 1 was charged in two reactors by 50 ml each and the temperature was elevated to 60° C. Et$_3$N was added respectively in 2-fold and 5-fold mole amounts to β-APM$_2$(L/L).HCl. Each mixture was reacted at 60° C. with stirring.

Each reaction mixture was subjected to sampling with passage of time and the α-AP derivatives were quantitatively determined by HPLC. The results are summarized in the following table.

| Et$_3$N (fold-mol) | | | Time (Hr) | |
|---|---|---|---|---|
| | | 6 | 24 | 30 |
| 2 | Yield of α-AP derivatives | 7.6(%) | 35.6(%) | 48.6(%) |
| | Details α-APM$_2$ | 7.1 | 22.2 | 26.7 |
| | DKPOMe | 0.5 | 13.4 | 21.9 |
| 5 | Yield of α-AP Derivatives | 20.3 | 52.4 | 65.5 |
| | Details α-APM$_2$ | 17.7 | 24.4 | 29.0 |
| | DKPOMe | 2.6 | 28.0 | 36.5 |

EXAMPLE 4

The MeOH solution of β-APM$_2$(L/L).HCl prepared in Example 1 was charged in three reactors by 50 ml each and the temperature of each solution was adjusted to 0°, 20° and 40° C., respectively. Et$_3$N was added to each solution in a 5-fold mole amount to β-APM$_2$(L/L).HCl. Each mixture was reacted at the respective temperatures previously adjusted, respectively.

Fourty-four hours after, the α-AP derivatives (α-APM$_2$+DKPOMe) were quantitatively determined by HPLC; in case that the reaction temperature was 0°, 20° and 40° C., the α-AP derivatives were formed in 1.0%, 15.9% and 60.4%, respectively.

Further 50 ml of the MeOH solution of β-APM$_2$(L/L).HCl prepared in Example 1 was charged in an autoclave and Et$_3$N was added in a 5-fold mole amount to β-APM$_2$(L/L).HCl. After thoroughly substituting with nitrogen gas, pressure was applied by nitrogen gas until the inner pressure reached 10 kg/cm$^2$ and, the system was sealed.

Thereafter, the mixture was reacted at 100° C. for 15 hours and the α-AP derivatives (α-APM$_2$+DKPOMe) were quantitatively determined by HPLC and formed in 89.2%.

EXAMPLE 5

In MeOH was dissolved 10 g of potassium hydroxide (hereafter merely referred to as KOH) to make 100 ml of a MeOH solution of KOH. The temperature of 50 ml of the MeOH solution of β-APM$_2$ (L/L).HCl prepared in Example 1 was elevated at 60° C. and 0.92 ml of the MeOH solution of KOH prepared above was added thereto. The mixture was reacted at 60° C. for 4 hours with stirring.

Thereafter, the α-AP derivatives (α-APM$_2$+DKPOMe+α-aspartylphenylalanine anhydride (hereafter simply referred to as DKP)) were quantitatively determined by HPLC and formed in 79.2%.

EXAMPLE 6

In water was dissolved 10.6 g of sodium carbonate (hereafter merely referred to as Na$_2$CO$_3$) to make 100 ml of an aqueous solution of Na$_2$CO$_3$. The temperature of 50 ml of the methanol solution of β-APM$_2$(L/L).HCl prepared in Example 1 was elevated to 60° C. and 2 ml of the aqueous solution of Na$_2$CO$_3$ prepared above was added thereto. The mixture was reacted at 60° C. for 8 hours with stirring.

Thereafter, the α-AP derivatives (α-APM$_2$+DKPOMe+DKP) were formed in 38.9% according to quantitative determination by HPLC.

On the other hand, the temperature of 50 ml of the MeOH solution of β-APM$_2$(L/L).HCl prepared in Example 1 was elevated to 60° C. and 217 mg of Na$_2$CO$_3$ crystals were added to the solution. The mixture was reacted at 60° C. for 8 hours with stirring while suspending. Thereafter, the α-AP derivatives (α-APM$_2$+DKPOMe+DKP) were quantitatively determined by HPLC and formed in 73.5%.

EXAMPLE 7

In water was dissolved 8.4 g of sodium hydrogen carbonate (hereafter merely referred to as NaHCO$_3$) to make 100 ml of an aqueous solution of NaHCO$_3$. The temperature of 50 ml of the MeOH solution of β-APM$_2$(L/L).HCl prepared in Example 1 was elevated to 60° C. and 4.1 ml of the aqueous solution of NaHCO$_3$ prepared above was added to the solution. The mixture was reacted at 60° C. for 8 hours with stirring.

Thereafter, the α-AP derivatives (α-APM$_2$+DKPOMe+DKP) were quantitatively determined by HPLC and formed in 69.8%.

On the other hand, the temperature of 50 ml of the MeOH solution of β-APM$_2$(L/L).HCl prepared in Example 1 was elevated to 60° C. and 344 mg of NaHCO$_3$ crystals were added to the solution. The mixture was reacted at 60° C. for 8 hours with stirring while suspending.

Thereafter, the α-AP derivatives (α-APM$_2$+DKPOMe) were quantitatively determined by HPLC and formed in 73.8%.

EXAMPLE 8

In MeOH was dissolved 2.58 g of β-A(M)P to make 500 ml of a MeOH solution of β-A(M)P. The temperature of 50 ml of the obtained MeOH solution of β-A(M)P was elevated to 60° C. and Et$_3$N was added to the solution until it reached a 4-fold amount based on β-A(M)P followed by reacting at 60° C. for 45 hours with stirring.

Quantitative determination of the α-AP derivatives, namely, α-aspartylphenylalanine-β-methyl ester (β-carboxyl group of the aspartic acid residue of α-aspartylphenylalanine is converted into methyl ester; hereafter simply referred to as α-A(M)P, and α-aspartylphenylalanine (hereafter simply referred to as α-AP)) revealed the formation in 28.4% in total.

EXAMPLE 9

The temperature of 50 ml of the MeOH solution of β-A(M))P prepared in Example 8 was elevated to 60° C. and 2.46 ml of the MeOH solution of KOH prepared in Example 5 was added to the solution. The mixture was reacted at 60° C. for 4 hours with stirring.

Thereafter, the α-AP derivatives (α-A(M)P+α-AP) were quantitatively determined by HPLC and formed in 19.0%.

EXAMPLE 10

In a manner similar to Example 4, 50 ml of the MeOH solution of β-APM$_2$(L/L).HCl prepared in Example 1 was reacted at 100° C. for 6 hours in an autoclave.

The α-AP derivatives (α-APM$_2$+DKPOMe) were quantitatively determined by HPLC and formed in 8.2%. Further in a similar manner, the reaction was performed in an autoclave at 120° C. for 6 hours to form 22.6% of the α-AP derivatives (α-APM$_2$+DKPOMe).

EXAMPLE 11

In an autoclave was charged 50 ml of the MeOH solution of β-APM$_2$(L/L).HCl prepared in Example 1. Acetic acid was added thereto in a 5-fold mole amount to β-APM$_2$(L/L).HCl. The mixture was reacted at 120° C. for 6 hours under the inner nitrogen pressure of 10 kg/cm$^2$ in a manner similar to Example 4.

Thereafter, the α-AP derivatives (α-APM$_2$+DKPOMe) were quantitatively determined by HPLC and formed in 35.2%.

EXAMPLE 12

In a solvent mixture of 40 ml of MeOH and 10 ml of ethyl acetate was dissolved 283.4 mg of β-APM$_2$(L/L).HCl. The temperature was elevated to 60° C. Et$_3$N was added in a 10-fold mole amount to β-APM$_2$(L/L).HCl. The mixture was reacted at 60° C. for 24 hours with stirring.

Thereafter, the α-AP derivatives (α-APM$_2$+DKPOMe) were quantitatively determined by HPLC and formed in 65.1%.

EXAMPLE 13

In ethyl alcohol was dissolved 306.5 mg of β-aspartylphenylalanine diethyl ester hydrochloride. The temperature of the solution was elevated to 60° C. Et₃N was added to the solution in a 10-fold mole amount to β-aspartylphenylalanine diethyl ester. The mixture was reacted at 60° C. for 24 hours with stirring.

Thereafter, the α-AP derivatives (α-aspartylphenylalanine diethyl ester and α-aspartylphenylalanine anhydride ethy ester) were quantitatively determined by HPLC and formed in 73.4%.

What is claimed is:

1. A method for converting β-aspartylphenylalanine derivative (1) to α-aspartylphenylalanine derivatives (2) and (3), said derivatives having the following structures:

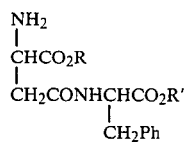

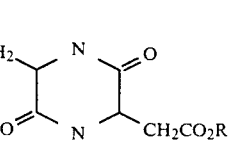

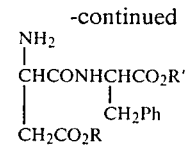

which comprises:
reacting said β-aspartylphenylalanine derivative (1) at a temperature of from 0° to 200° C. for a time period of from 30 minutes to 80 hours, in a $C_1$ to $C_4$ alcohol solvent with or without stirring, wherein R and R' represent hydrogen or an alkyl group having from 1 to 4 carbon atoms.

2. The method according to claim 1 wherein R and R' are hydrogen or a methyl group.

3. The method according to claim 1 wherein said maintaining the β-aspartylphenylalanine derivative in an alcohol solvent is performed in the presence of an acid or a basic catalyst.

* * * * *

UNITED STATES PATENT AND TRADEMARK OFFICE
CERTIFICATE OF CORRECTION

PATENT NO. : 4,673,744

DATED : June 16, 1987

INVENTOR(S) : Hisamitsu et al.

It is certified that error appears in the above-identified patent and that said Letters Patent is hereby corrected as shown below:

On the Title Page [Item 75] Inventors:

--The first joint inventor was also recorded as the fourth joint inventor. The fourth joint inventor, Kunio Hisamitsu, should be deleted.--

Signed and Sealed this

Twentieth Day of October, 1987

Attest:

DONALD J. QUIGG

*Attesting Officer*  *Commissioner of Patents and Trademarks*